(12) United States Patent
Ikeda et al.

(10) Patent No.: US 11,832,980 B2
(45) Date of Patent: Dec. 5, 2023

(54) RADIOGRAPHY APPARATUS

(71) Applicant: FUJIFILM Corporation, Tokyo (JP)

(72) Inventors: Yuji Ikeda, Ashigarakami-gun (JP); Masahito Sambuichi, Ashigarakami-gun (JP); Hisatsugu Horiuchi, Ashigarakami-gun (JP); Masayoshi Matsuura, Ashigarakami-gun (JP); Ryo Imamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 472 days.

(21) Appl. No.: 17/210,870

(22) Filed: Mar. 24, 2021

(65) Prior Publication Data

US 2021/0204891 A1 Jul. 8, 2021

Related U.S. Application Data

(63) Continuation of application No. PCT/JP2019/037928, filed on Sep. 26, 2019.

(30) Foreign Application Priority Data

Sep. 27, 2018 (JP) .................. 2018-182999

(51) Int. Cl.
*A61B 6/00* (2006.01)
(52) U.S. Cl.
CPC .......... *A61B 6/4441* (2013.01); *A61B 6/4208* (2013.01); *A61B 6/4405* (2013.01); *A61B 6/4452* (2013.01)
(58) Field of Classification Search
CPC ................ A61B 6/4441; A61B 6/4208; A61B 6/4405; A61B 6/4452; A61B 6/4411; A61B 6/08;
(Continued)

(56) References Cited

U.S. PATENT DOCUMENTS 7,039,162 B2 * 5/2006 Ikeda ............... A61B 6/585
378/98.8
9,049,996 B2 * 6/2015 Tsujii ................ A61B 6/4007
(Continued)

FOREIGN PATENT DOCUMENTS

JP 2005-13705 A 1/2005
JP 2006-311929 A 11/2006
(Continued)

OTHER PUBLICATIONS

International Preliminary Report on Patentability and Written Opinion of the International Searching Authority, with an English translation (forms PCT/IB/373, PCT/ISA/237 and PCT/IB/326), dated Apr. 8, 2021, for corresponding International Application No. PCT/JP2019/037928.
(Continued)

*Primary Examiner* — David P Porta
*Assistant Examiner* — Gisselle M Gutierrez
(74) *Attorney, Agent, or Firm* — Birch, Stewart, Kolasch & Birch, LLP

(57) ABSTRACT

A radiography apparatus includes an operation controller that invalidates an operation of a collimator using a first operating unit in a case where a radiation generation unit is present vertically downward relatively to a radiography unit, and validates the operation of the collimator using the first operating unit in a case where the radiation generation unit is present vertically upward relatively to the radiography unit.

19 Claims, 10 Drawing Sheets

(58) Field of Classification Search
CPC ........... A61B 6/486; A61B 6/545; A61B 6/06;
A61B 6/5252; A61B 6/54; A61B 6/547;
A61B 6/582; A61B 6/586; A61B 6/587;
A61B 6/588
See application file for complete search history.

(56) References Cited

U.S. PATENT DOCUMENTS

| | | | |
|---|---|---|---|
| 11,690,588 B2 * | 7/2023 | Kitano | ............... A61B 6/488 378/62 |
| 2010/0098215 A1 | 4/2010 | Takahashi | |
| 2019/0380668 A1 * | 12/2019 | Richard | ................ A61B 6/10 |
| 2023/0087238 A1 * | 3/2023 | Broad | ............... A61N 5/1075 |

FOREIGN PATENT DOCUMENTS

| | | |
|---|---|---|
| JP | 2006-320496 A | 11/2006 |
| JP | 2010-94369 A | 4/2010 |
| JP | 2013-128593 A | 7/2010 |
| WO | WO 2014/132360 A1 | 9/2014 |

OTHER PUBLICATIONS

International Search Report (form PCT/ISA/210), dated Nov. 5, 2019, for corresponding International Application No. PCT/JP2019/037928, with an English translation.

* cited by examiner

RADIOGRAPHY APPARATUS

CROSS-REFERENCE TO RELATED APPLICATIONS

This application is a Continuation of PCT International Application No. PCT/JP2019/037928 filed on 26 Sep. 2019, which claims priority under 35 U.S.C. § 119(a) to Japanese Patent Application No. 2018-182999 filed on 27 Sep. 2018. The above application is hereby expressly incorporated by reference, in its entirety, into the present application.

BACKGROUND OF THE INVENTION

1. Field of the Invention

The present invention relates to a radiography apparatus.

2. Description of the Related Art

Some radiography apparatuses support a radiation source configured to generate radiation and a radiography unit configured to image subject using radiation with one arm, and define a relative positional relationship of the radiation source and the radiography unit is known. For example, an X-ray imaging apparatus that supports an X-ray source and an X-ray imaging panel with a C-arm is known.

In recent years, among the radiography apparatuses that support the radiation source and the radiography unit with one arm, a radiography apparatus that performs radiography in a state in which the radiation source or the radiography unit is detached from the arm is known (JP2013-128593A).

SUMMARY OF THE INVENTION

In a case where the radiation source and the radiography unit are supported with one arm, relative positions of the radiation source and the radiography unit are fixed, and thus, there is an advantage that alignment of the radiation source and the radiography unit is not required.

Note that, in the radiography apparatus that supports the radiation source and the radiography unit with one arm, a person or an object unintentionally comes into contact with an operating unit provided in the arm depending on the position of the radiation source or the like in a case where the arm is operated, and inconvenience that imaging conditions adjusted once need to be readjusted, or the like may occur.

Furthermore, even though the radiation source or the radiography unit is detached from the arm and used, it is still inconvenient that there are a large number of adjustment items, or the like depending on the disposition of the radiation source or the radiography unit compared to a radiography apparatus that supports a radiation source and a radiography unit with separate arms.

Accordingly, an object of the invention is to provide a radiography apparatus that eliminates inconvenience of a radiography apparatus capable of supporting a radiation source and a radiography unit with one arm and improves convenience.

A radiography apparatus of the invention comprises a radiation generation unit having a radiation source configured to generate radiation, a collimator configured to adjust an irradiation range of the radiation, and a first operating unit configured to operate the collimator, a radiography unit that images a subject using the radiation, a support that supports at least the radiation generation unit in a case where the subject is imaged, and an operation controller that invalidates an operation of the collimator using the first operating unit in a case where the radiation generation unit is present vertically downward relatively to the radiography unit, and validates the operation of the collimator using the first operating unit in a case where the radiation generation unit is present vertically upward relatively to the radiography unit.

Another radiography apparatus of the invention comprises a radiation generation unit having a radiation source configured to generate radiation, a collimator configured to adjust an irradiation range of the radiation, and a first operating unit configured to operate the collimator, a radiography unit that images a subject using the radiation, a support that supports at least the radiation generation unit in a case where the subject is imaged, and an operation controller that validates an operation of the collimator using the first operating unit in a static image capturing mode where a static image of the subject is captured, and invalidates the operation of the collimator using the first operating unit in a video capturing mode where video of the subject is captured.

It is preferable that another radiography apparatus of the invention comprises a radiation generation unit having a radiation source configured to generate radiation, a collimator configured to adjust an irradiation range of the radiation, and a first operating unit configured to operate the collimator, a radiography unit that images a subject using the radiation, a support that supports at least the radiation generation unit in a case where the subject is imaged, and an operation controller that invalidates an operation by the first operating unit in a case where the radiography unit is attached to the support, and validates the operation by the first operating unit in a case where the radiography unit is not attached to the support.

It is preferable that the radiography apparatus comprises a posture detection unit that detects a posture of the support, and the operation controller obtains information regarding a position of the radiation generation unit using a detection result of the posture detection unit.

It is preferable that the collimator comprises a first restriction unit that restricts the irradiation range of the radiation, and a second restriction unit that further restricts the irradiation range of the radiation restricted by the first restriction unit, and the first operating unit is an operating unit that operates the second restriction unit.

It is preferable that the radiography apparatus further comprises a drive controller that automatically drives the first restriction unit, and the drive controller relaxes the restriction of the irradiation range of the radiation by the first restriction unit in a case where the operation controller validates the operation using the first operating unit, compared to a case where the operation controller invalidates the operation using the first operating unit.

It is preferable that the second operating unit that operates the collimator is provided in a body to which the support is attached.

It is preferable that the radiography apparatus further comprises a rotational movement controller that validates or invalidates rotational movement of the radiation generation unit with respect to the support.

It is preferable that the radiography apparatus further comprises an irradiation range display unit that displays the irradiation range of the radiation adjusted by the collimator using visible light, and a display controller that validates or invalidates the display of the irradiation range of the radiation by the irradiation range display unit depending on a position of the radiation generation unit.

According to the invention, it is possible to provide a radiography apparatus that eliminates inconvenience of a radiography apparatus capable of supporting a radiation source and a radiography unit with one arm, and improves convenience.

DESCRIPTION OF THE PREFERRED EMBODIMENTS

Figure 1:
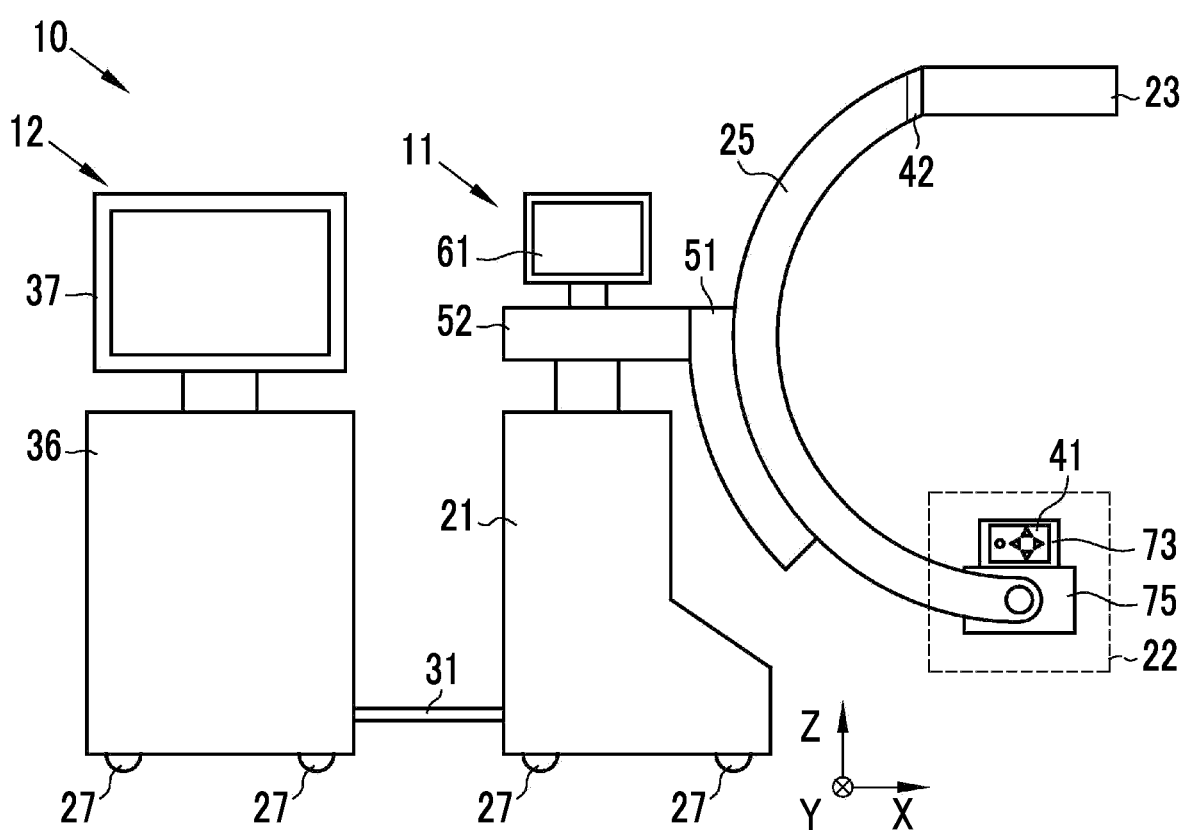
FIG. 1 is a schematic view of a radiography apparatus.

As shown in FIG. 1, a radiography apparatus 10 comprises an imaging unit 11 and a display unit 12. The imaging unit 11 is a unit that generates radiation and images a subject 15 (see FIG. 4) using the radiation. The display unit 12 is a unit that displays or the like a radiographic image captured using the imaging unit 11.

The imaging unit 11 comprises an imaging unit body 21, a radiation generation unit 22, a radiography unit 23, and a C-arm 25.

The imaging unit body 21 integrally controls the operations of the radiation generation unit 22, the radiography unit 23, the C-arm 25, and the like. The imaging unit body 21 is connected to the display unit 12 in a wired or wireless manner. In the embodiment, the imaging unit body 21 is connected to the display unit 12 using a cable 31 in a wired manner. With this, the imaging unit 11 supplies a radiographic image, electric power, and the like to the display unit 12. The display unit 12 comprises a display unit body 36, and a monitor 37 that displays a radiographic image or the like. A caster 27 is attached to the imaging unit body 21 and the display unit body 36. For this reason, the radiography apparatus 10 is movable, and can perform radiography in a patient's room where a patient who is the subject 15 is present.

The radiation generation unit 22 generates radiation in a case of performing radiography. The radiation generation unit 22 is rotationally movably attached to one end of the C-arm 25. In the embodiment, the rotational movement of the radiation generation unit 22 is possible within a plane of the C-arm 25. For example, in a case where the C-arm 25 is disposed within an XZ plane (see FIG. 1), the radiation generation unit 22 can be rotationally moved in an XZ in-plane direction. Furthermore, the radiation generation unit 22 comprises a first operating unit 41. The first operating unit 41 is an operating unit that is provided to operate the radiation generation unit 22, and may be validated or invalidated according to the usages of the radiography apparatus 10. In the embodiment, although the radiation that is generated in the radiation generation unit 22 is X-rays, the radiation generation unit 22 can be substituted with a configuration of generating radiation other than X-rays.

The radiography unit 23 is attachably and detachably to the other end (an end portion opposite to the end portion to which the radiation generation unit 22 is attached) of the C-arm 25. The radiography unit 23 images the subject 15 using the radiation generated by the radiation generation unit 22. The attachment and detachment detection unit 42 is a mechanism that detects attachment and detachment of the radiography unit 23, and is, for example, a switch mechanism that is turned on in a case where the radiography unit 23 is attached. The attachment and detachment detection unit 42 is incorporated in the end portion of the C-arm 25 attached to the radiography unit 23 in the embodiment. The attachment and detachment of the radiography unit 23 includes attachment and detachment of a part of components of the radiography unit 23. The attachment and detachment detection unit 42 can detect a size (so-called panel size) of an effective detection region 81 (see FIG. 8) of the radiography unit 23 in addition to the attachment and detachment of the radiography unit 23.

In principle, the C-arm 25 is held at a position (hereinafter, referred to as a confronting position) where the radiation generation unit 22 confronts the radiography unit 23. That is, the C-arm 25 constitutes a support that supports at least the radiation generation unit 22 in a case of imaging the subject. Specifically, the C-arm 25 holds the radiation generation unit 22 and the radiography unit 23 at the confronting position in a case where both the radiation generation unit 22 and the radiography unit 23 are attached. Note that the radiography apparatus 10 can detach the radiography unit 23 from the C-arm 25 to perform radiography. Accordingly, in a case where the radiography unit 23 is detached from the C-arm 25 to perform radiography, the C-arm 25 holds the radiation generation unit 22 at any position and in any orientation (normally, a position confronting the radiography unit 23). The confronting position is a position where the radiography unit 23 can capture the radiation generated by the radiation generation unit 22 substantially vertically. The term "substantially vertically" allows an inclination or the like of at least one of the radiation generation unit 22 or the radiography unit 23 without causing trouble in imaging of the subject 15.

The C-arm 25 is connected to a lifting mechanism 52 through a sliding mechanism 51. The sliding mechanism 51 holds the C-arm 25 in a slidable (slidingly movable) manner in an arc shape. As the C-arm 25 is slid by the sliding mechanism 51, the radiation generation unit 22 and the radiography unit 23 can be rotated around the center (the center of a "C" shape that is an arc) of the C-arm 25 while maintaining the confronting position. For example, in a case where the radiation generation unit 22 and the radiography unit 23 are disposed within the XZ plane as shown in FIG. 1, as the C-arm 25 is slid using the sliding mechanism 51, the C-arm 25, and the radiation generation unit 22 and the radiography unit 23 attached to the C-arm 25 can be rotated around the Y-axis.

The sliding mechanism 51 is rotatably attached to the lifting mechanism 52 liftably attached to the imaging unit body 21 in a vertical direction (Z-axis direction). For this reason, the C-arm 25 is rotatable around a specific direction (X-axis) within a horizontal plane. As the lifting mechanism 52 is lifted up and down, the C-arm 25, and the radiation generation unit 22 and the radiography unit 23 attached to the C-arm 25 can be optionally moved vertically upward (Z-axis positive direction) or vertically downward (Z-axis negative direction).

In addition to the above-described configuration, the imaging unit body 21 comprises a second operating unit 61. The second operating unit 61 is an operating unit that operates the respective units of the imaging unit body 21 including the radiation generation unit 22. That is, the second operating unit 61 is an operating unit that can operate at least a collimator 73, and is provided in the imaging unit body 21 attached to the C-arm 25 as a support. An operation using the second operating unit 61 is valid regardless of validation or invalidation of the first operating unit 41. An operation of each unit, such as the collimator 73, using the second operating unit 61 can be performed at any timing.

Figure 2:
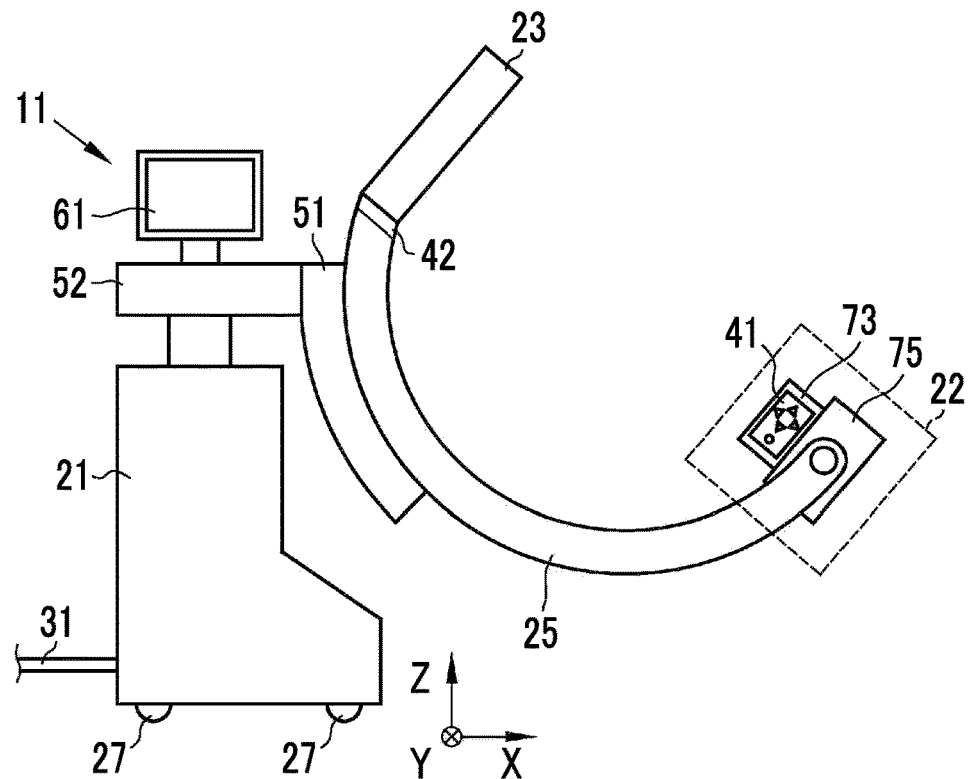
FIG. 2 shows the radiography apparatus in which a C-arm is slid.
Figure 3:
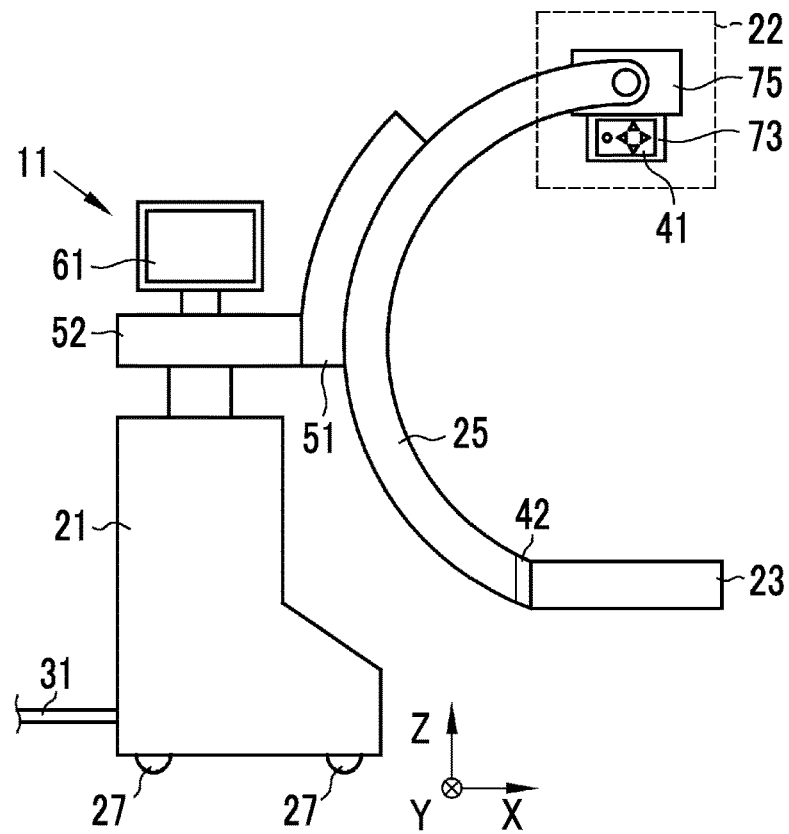
FIG. 3 shows the radiography apparatus in which the C-arm is rotated.
Figure 4:
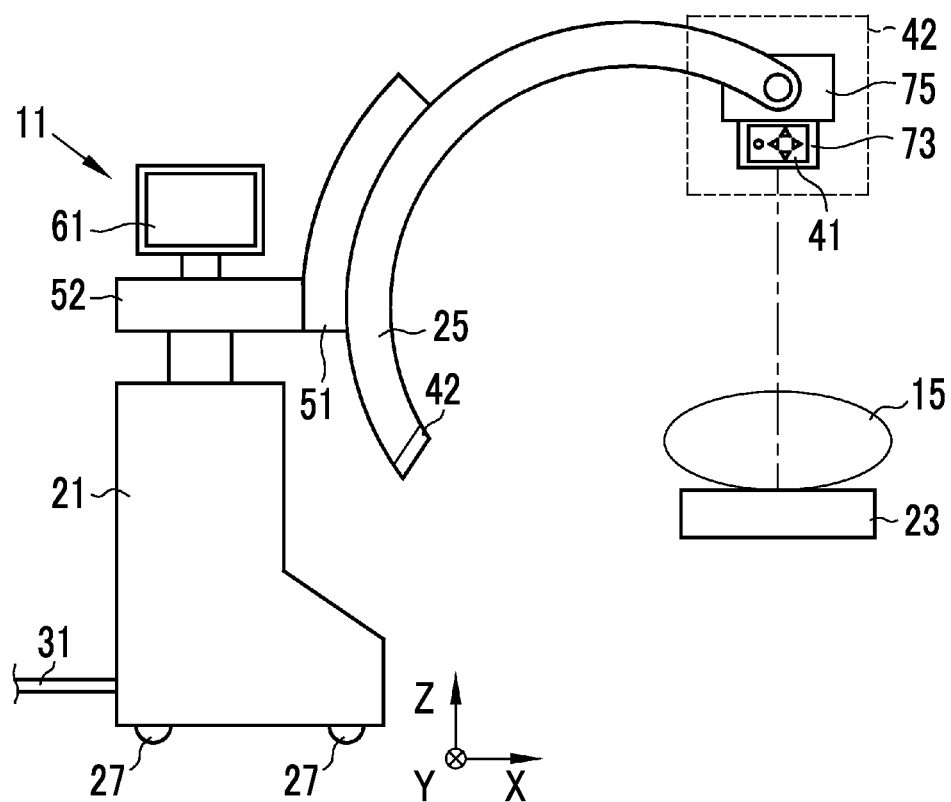
FIG. 4 is a schematic view in a case where a radiography panel is separated to perform imaging.

The radiography apparatus 10 configured as described above can image the subject 15 in a form of a static image or video using radiation. That is, the radiography apparatus 10 has a static image capturing mode in which a static image of the subject 15 is captured using radiation, and a video capturing mode in which video of the subject 15 is captured using radiation. In the embodiment, as shown in FIGS. 1 and 2, capturing of video is performed by disposing the radiation generation unit 22 substantially vertically downward (Z-axis negative direction) relatively to the radiography unit 23 and disposing the radiography unit 23 substantially vertically upward (Z-axis positive direction) relatively to the radiation generation unit 22. On the other hand, as shown in FIGS. 3 and 4, capturing of a static image is performed by disposing the radiation generation unit 22 substantially vertically upward relatively to the radiography unit 23. Furthermore, as shown in FIG. 4, capturing of a static image can be performed in a state in which the radiography unit 23 is detached from the C-arm 25. In this case, the radiography unit 23 is disposed behind the subject 15 (in FIG. 4, on a Z-direction negative side of the subject 15) as viewed from the radiation generation unit 22.

Figure 5:
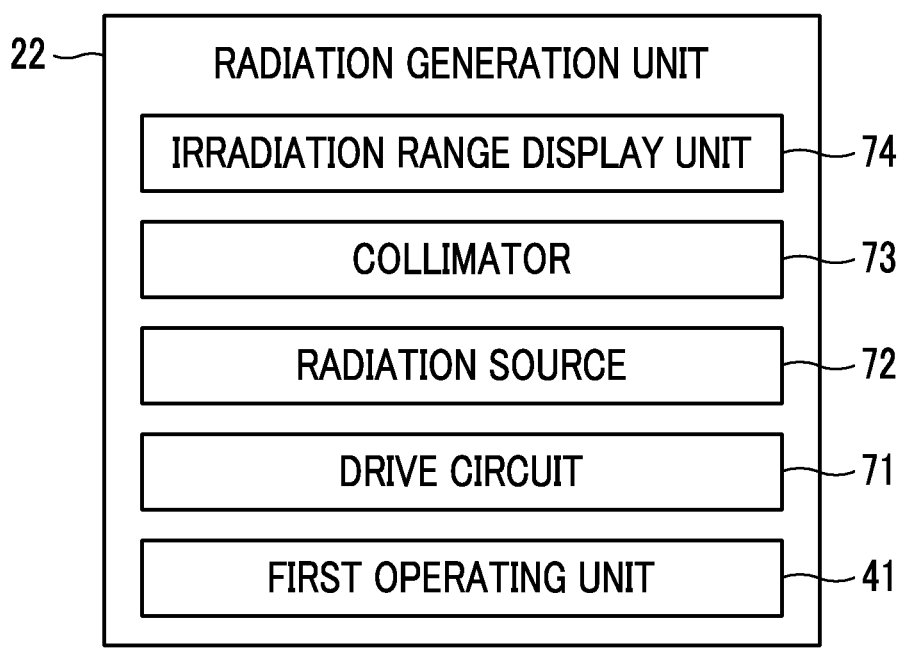
FIG. 5 is a block diagram of a radiation generation unit.

As shown in FIG. 5, the radiation generation unit 22 comprises a drive circuit 71, a radiation source 72, the collimator 73, an irradiation range display unit 74, and the first operating unit 41.

The drive circuit 71 is a drive circuit that drives the radiation source 72, and is a so-called high-voltage generation circuit. The drive circuit 71 supplies electric power needed to generate radiation to the radiation source 72. A high voltage in the drive circuit 71 refers to a voltage needed for the radiation source 72 to generate radiation.

The radiation source 72 receives supply of needed electric power from the drive circuit 71 to generate radiation. In the embodiment, the radiation source 72 is an X-ray source that generates X-rays. In the embodiment, the radiation source 72 is integrated with the drive circuit 71, and constitutes a so-called mono-tank 75 (see FIG. 1).

The collimator 73 is a mechanism that adjusts an irradiation range of the radiation generated by the radiation source 72. In the radiography apparatus 10, the irradiation range of the radiation can be appropriately changed according to conditions or the like of imaging using the collimator 73. The collimator 73 is disposed in a direction (the radiography unit 23 side) in which the radiation source 72 (mono-tank 75) emits the radiation.

Figure 6:
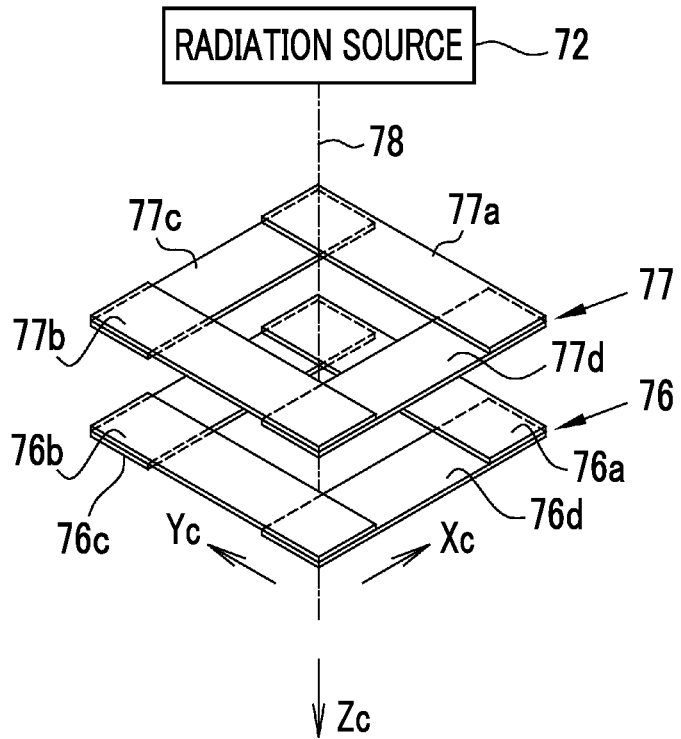
FIG. 6 is a perspective view showing the configuration of a collimator.

As shown in FIG. 6, the collimator 73 comprises a second restriction unit 77 and a first restriction unit 76 in order from the radiation source 72 along a radiation direction (hereinafter, referred to as a radiation axis) 78 of the radiation generated by the radiation source 72. The first restriction unit 76 restricts the irradiation range of the radiation emitted from the radiation source 72. The second restriction unit 77 further restricts the irradiation range of the radiation restricted by the first restriction unit 76 within the range. That is, the first restriction unit 76 decides the outline of the irradiation range of the radiation. Then, the second restriction unit 77 further adjusts at least one of the size, the shape, or the like of the irradiation range within the irradiation range of the radiation defined by the first restriction unit 76.

The first restriction unit 76 comprises a first outer leaf blade 76a, a second outer leaf blade 76b, a third outer leaf blade 76c, and a fourth outer leaf blade 76d that shield the radiation. The first outer leaf blade 76a and the second outer leaf blade 76b are movable in a third direction (in FIG. 6, a positive or negative direction of an arrow Xc) perpendicular to the radiation axis 78. Furthermore, the third outer leaf blade 76c and the fourth outer leaf blade 76d are movable in a fourth direction (in FIG. 6, a positive or negative direction of an arrow Yc) perpendicular to the radiation axis 78 and perpendicular to a first direction. Accordingly, the first restriction unit 76 adjusts a position, a shape, and a size of an opening to be formed by the outer leaf blades 76a to 76d by adjusting positions of the outer leaf blades 76a to 76d. In the embodiment, the outer leaf blades 76a to 76d can be controlled independently. Note that at least one of the first outer leaf blade 76a and the second outer leaf blade 76b in a pair or the third outer leaf blade 76c and the fourth outer leaf blade 76d can be controlled in a pair.

Similarly, the second restriction unit 77 comprises a first inner leaf blade 77a, a second inner leaf blade 77b, a third inner leaf blade 77c, and a fourth inner leaf blade 77d that shields the radiation. The first inner leaf blade 77a and the second inner leaf blade 77b are movable in the first direction (in FIG. 6, a positive or negative direction of an arrow Xc) perpendicular to the radiation axis 78. Furthermore, the third inner leaf blade 77c and the fourth inner leaf blade 77d are movable in a second direction (in FIG. 6, a positive or negative direction of an arrow Yc) perpendicular to the radiation axis 78 and perpendicular to the first direction. Accordingly, the second restriction unit 77 adjusts a position, a shape, and a size of an opening to be formed by the inner leaf blades 77a to 77d by adjusting positions of the inner leaf blades 77a to 77d. As a result, the irradiation range of the radiation is restricted by the opening formed by the inner leaf blades 77a to 77d. As a result, the second restriction unit 77 can further restrict the irradiation range of the radiation restricted by the first restriction unit 76 as needed. In the embodiment, although the inner leaf blades 77a to 77d can be controlled independently, the first inner leaf blade 77a and the second inner leaf blade 77b may be controlled in a pair control such that the opening is opened or closed. Similarly, the third inner leaf blade 77c and the fourth inner leaf blade 77d may be controlled in a pair such that the opening is opened or closed.

Figure 7:
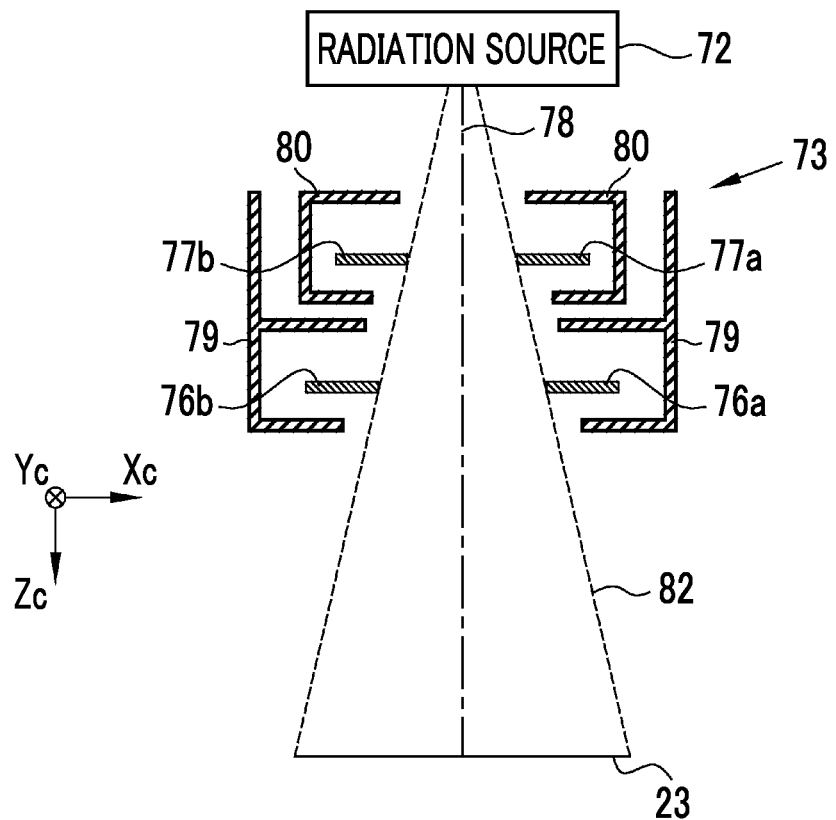
FIG. 7 is a sectional view showing the configuration of the collimator.
Figure 8:
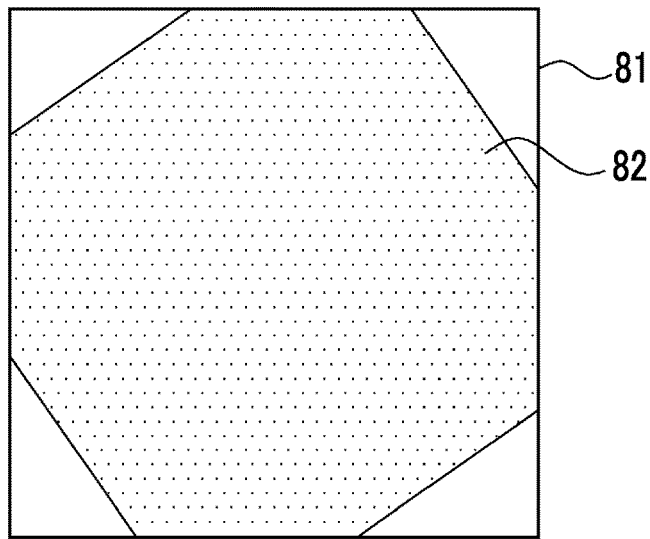
FIG. 8 is an explanatory view showing an effective detection region and an irradiation range of radiation.

As shown in FIG. 7, the collimator 73 has a nested structure in which a second housing 80 configured to store the inner leaf blades 77a to 77d constituting the second restriction unit 77 are housed in a first housing 79 configured to store the outer leaf blades 76a to 76d constituting the first restriction unit 76. Then, the second housing 80 is rotatable around the radiation axis 78 in the first housing 79. For this reason, as shown in FIG. 8, an irradiation range 82 of the radiation can be maintained within the effective detection region 81 in the radiography unit 23. The effective detection region 81 is a range in which the radiography unit 23 can detect radiation contributing to a radiographic image.

The first operating unit 41 is an operating unit that is provided to operate the second restriction unit 77. "Operating the second restriction unit 77" refers to adjusting the positions of the first inner leaf blade 77a, the second inner leaf blade 77b, the third inner leaf blade 77c, and the fourth inner leaf blade 77d, and rotating all inner leaf blades 77a to 77d around the radiation axis 78 along with the second housing 80.

The irradiation range display unit 74 is a light emitting element, such as a light emitting diode or a lamp, and irradiates the subject 15 with visible light from the vicinity of substantially a generation point (so-called focus) of X-rays through the collimator 73. With this, the irradiation range display unit 74 displays the irradiation range of the radiation adjusted by the collimator 73 on the subject 15 using visible light. The first operating unit 41 may be an operating unit that turns on or off the light emitting element of the irradiation range display unit 74. That is, the first operating unit 41 including an operation button or the like that turns on or off the display of the irradiation range.

The first operating unit 41 is a controller that is provided to control the respective units of the radiation generation unit 22. Specifically, the first operating unit 41 is an operating unit of the collimator 73 and the irradiation range display unit 74. Accordingly, a physician or the like who is a user can adjust the irradiation range of the radiation by operating the first operating unit 41. Furthermore, the physician or the like can turn on or off the display of the irradiation range of the radiation by operating the first operating unit 41. The first operating unit 41 is provided in, for example, the collimator 73 (see FIG. 1 or the like).

Figure 9:
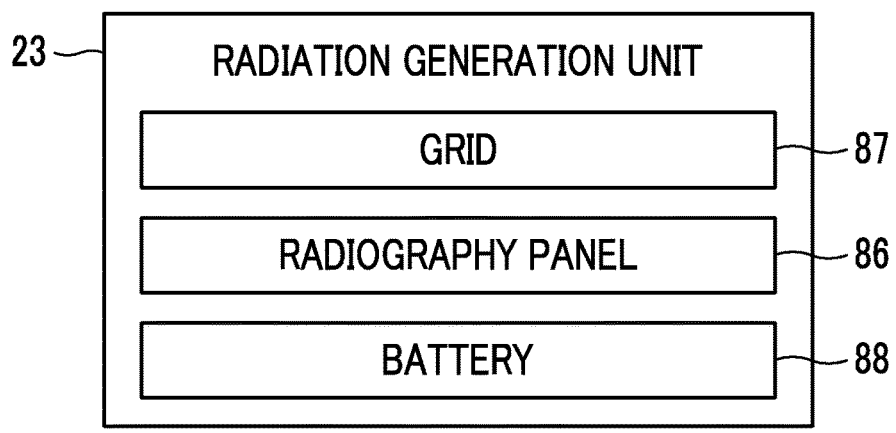
FIG. 9 is a block diagram of a radiography unit.

As shown in FIG. 9, the radiography unit 23 comprises a radiography panel 86, a grid 87, a battery 88, and the like.

The radiography panel 86 receives the radiation generated by the radiation generation unit 22 to image the subject 15. That is, the radiography panel 86 (or the entire radiography unit 23) is a so-called direct conversion type or indirect conversion type flat panel detector (FPD). In the embodiment, the radiography panel 86 included in the radiography unit 23 can be replaced with another radiography panel that is different in panel size or the like.

The grid 87 is a member that improves resolution or the like of a radiographic image by eliminating scattered rays, and is disposed on an incidence side (a side on which the radiation generation unit 22 is present) of the radiation of the radiography panel 86. The grid 87 can be replaced. The replacement of the grid 87 can be performed along with the radiography panel 86 or separately from the radiography panel 86. The grid 87 can be included in the radiography panel 86.

The battery 88 is a power supply that supplies electric power to the radiography panel 86. The battery 88 can be included in the radiography panel 86. In the embodiment, since the radiography unit 23 can be detached from the C-arm 25 and used, the radiography unit 23 is mounted with the battery 88. Meanwhile, in the radiography apparatus 10, a radiography panel that is attached to the C-arm 25 and receives supply of electric power from the imaging unit body 21 to perform radiography can also be used. In this case, the radiography unit 23 can omit the battery 88.

Figure 10:
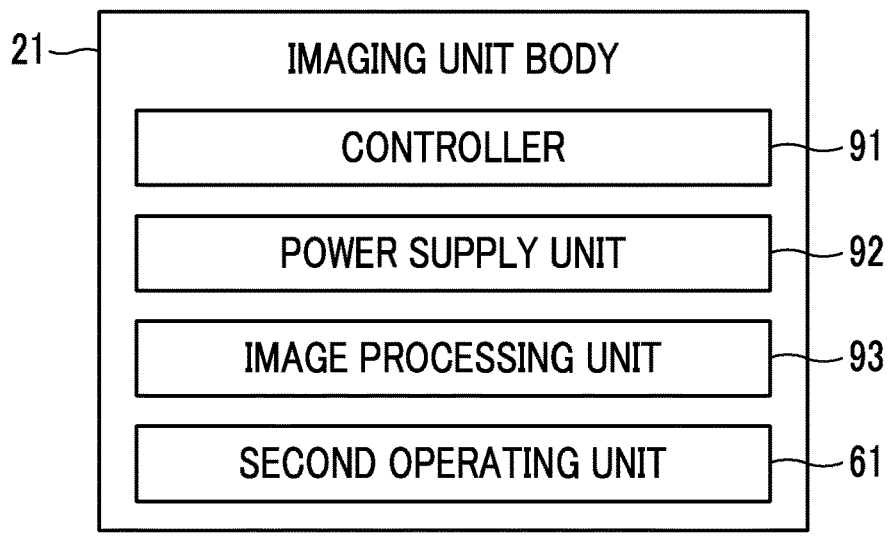
FIG. 10 is a block diagram of an imaging unit body.

As shown in FIG. 10, the imaging unit body 21 comprises, in addition to the second operating unit 61, a controller 91 that integrally controls the operations of the respective units of the radiography apparatus 10, a power supply unit 92 that supplies electric power to the respective units of the radiography apparatus 10, and an image processing unit 93 that executes image processing on a radiographic image captured using the radiography unit 23 as needed. In the embodiment, although the imaging unit body 21 comprises the image processing unit 93, the image processing unit 93 can be provided in the display unit body 36.

Figure 11:
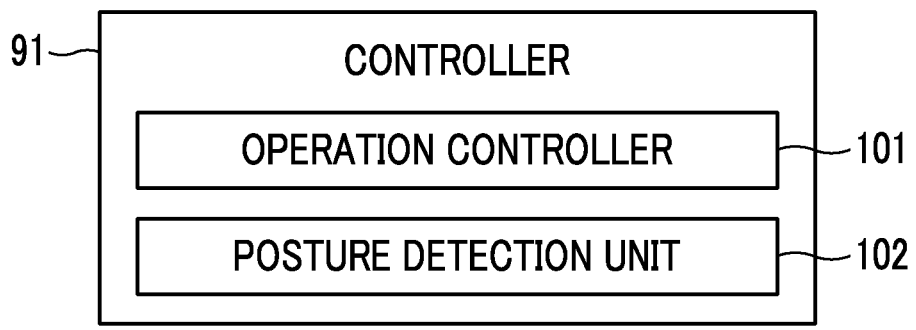
FIG. 11 is a block diagram of a controller.

As shown in FIG. 11, the controller 91 comprises an operation controller 101 and a posture detection unit 102.

Figure 12:
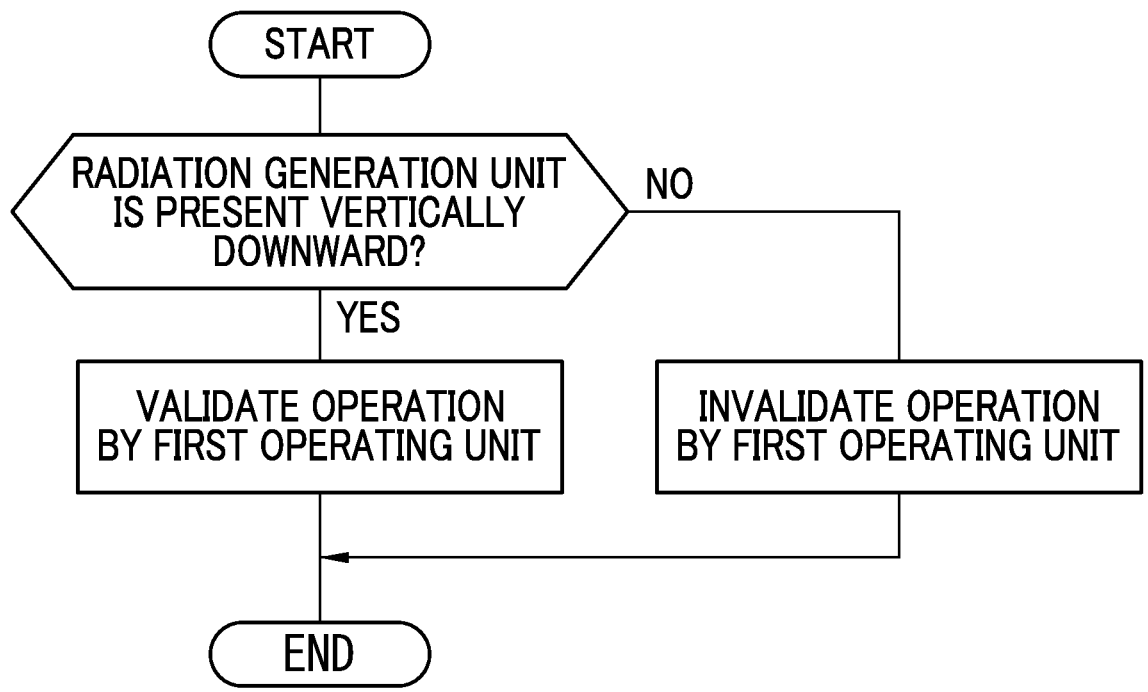
FIG. 12 is a flowchart showing operation.
Figure 13:
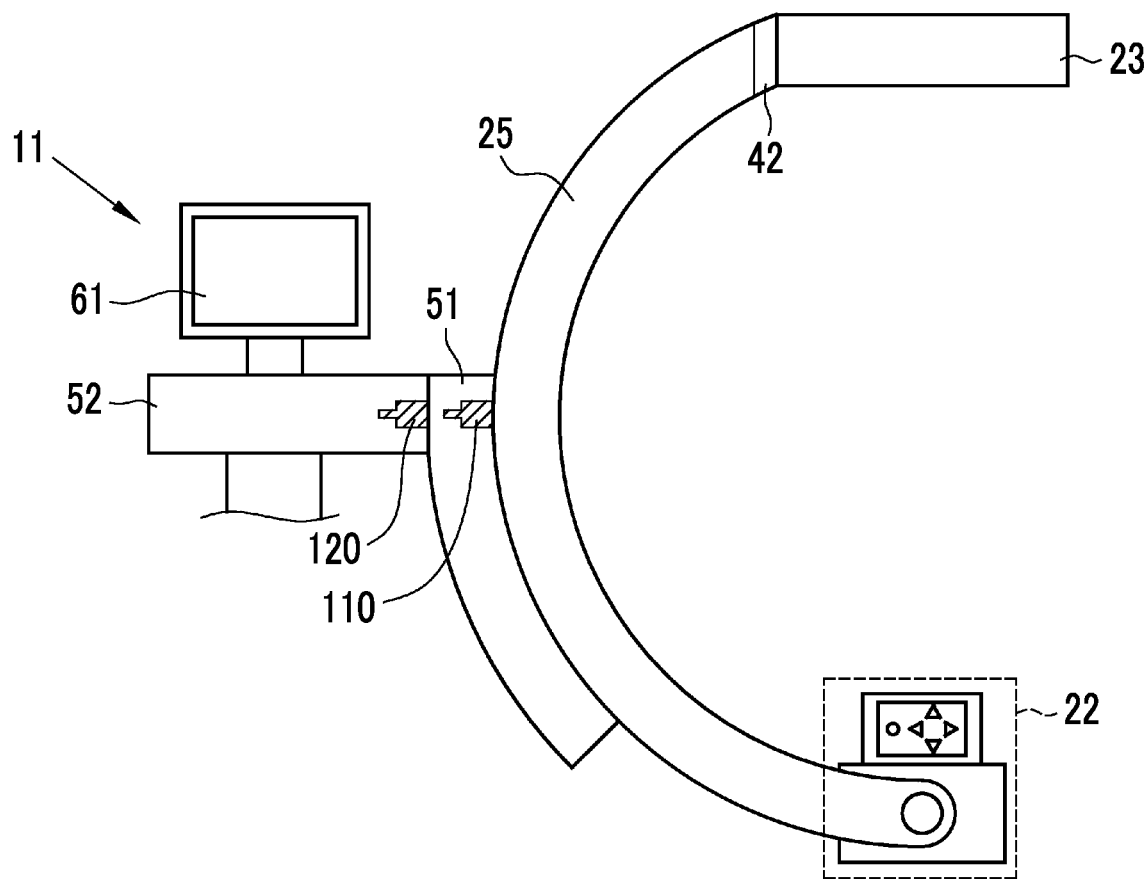
FIG. 13 is an explanatory view showing a configuration of detecting a posture of the C-arm.

The operation controller 101 validates or invalidates an operation of the collimator 73 using the first operating unit 41 depending on the position of the radiation generation unit 22. For example, as shown in FIG. 12, the operation controller 101 invalidates the operation of the collimator 73 using the first operating unit 41 in a case where the radiation generation unit 22 is present vertically downward (Z-axis negative direction) relatively to the radiography unit 23. On the other hand, the operation controller 101 validates the operation of the collimator 73 using the first operating unit 41 in a case where the radiation generation unit 22 is present vertically upward (Z-axis positive direction) relatively to the radiography unit 23.

The operation controller 101 acquires information regarding the position of the radiation generation unit 22 using a detection result of the posture detection unit 102. The posture detection unit 102 detects a posture of the C-arm 25 as a support using an output value of a first potentiometer 110 that measures a sliding amount of the C-arm 25 and an output value of a second potentiometer 120 that measures a rotation amount of the C-arm 25 (sliding mechanism 51). Furthermore, the posture detection unit 102 detects whether or not the radiography unit 23 is attached to the C-arm 25 using an output signal of the attachment and detachment detection unit 42, or the like. As a result of such detection, in a case where the radiography unit 23 is attached to the C-arm 25, the posture detection unit 102 can detect which of the radiation generation unit 22 and the radiography unit 23 is present relatively vertically upward depending on the posture of the C-arm 25.

As described above, in the radiography apparatus 10, the operation controller 101 validates or invalidates the operation of the collimator 73 using the first operating unit 41 attached to the radiation generation unit 22 depending on the position of the radiation generation unit 22. In a radiography apparatus (comparative example) of the related art that does not perform such control, for example, in a case where radiography is performed through the radiation generation unit 22 below a bed on which the subject 15 lies, the first operating unit 41 may come into contact with the bed or a staff or other objects in the periphery of the bed. For this reason, in the radiography apparatus of the comparative example, in a case where the first operating unit 41 that operates the collimator 73 comes into contact with the bed or the like, the irradiation range 82 of the radiation is unintentionally changed, and thus, it is inconvenient that readjustment is required. In contrast, in the above-described radiography apparatus 10, in an imaging form in which the radiation generation unit 22 is present vertically downward, and the radiation generation unit 22 including the first operating unit 41 is likely to pass under the bed or the like, the operation controller 101 invalidates the operation of the collimator 73 by the first operating unit 41. For this reason, in the radiography apparatus 10, even though the first operating unit 41 comes into contact with the bed or the like, the setting of the collimator 73 is not unintentionally changed. As a result, the readjustment of the collimator 73 does not occur, and thus, the radiography apparatus 10 is excellent in convenience compared to the radiography apparatus of the comparative example. During an operation of the subject 15, there is a case where radiography is repeated any number of times, and the number of times in which the radiation generation unit 22 passes under the bed or the like also increases. Thus, the radiography apparatus 10 is particularly suitable for such a case.

Figure 14:
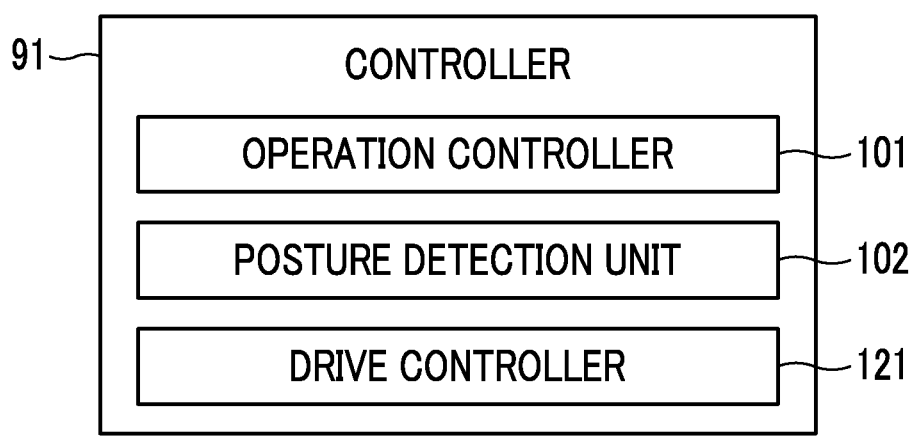
FIG. 14 is a block diagram of a controller having a drive controller.

As shown in FIG. 14, the controller 91 of the radiography apparatus 10 can comprise a drive controller 121 instead of at least one of the operation controller 101 or the posture detection unit 102 or in addition to at least one of the operation controller 101 or the posture detection unit 102.

For example, the drive controller 121 is provided in the controller 91 in addition to the operation controller 101. The drive controller 121 automatically drives the first restriction unit 76 of the collimator 73. Specifically, in a case where the operation controller 101 validates the operation using the first operating unit 41, the drive controller 121 relaxes the restriction to the irradiation range of the radiation by the first restriction unit 76 compared to a case where the operation controller 101 invalidates the operation using the first operating unit 41. In a case where control of the second restriction unit 77 by the first operating unit 41 is valid, for example, the drive controller 121 opens the opening of the first restriction unit 76 to a maximum, and restricts the irradiation range of the radiation substantially only with the second restriction unit 77. This is because the adjustment of the irradiation range of the radiation by the first restriction unit 76 is not required in the static image capturing mode (in particular, a case where the radiography unit 23 is detached from the C-arm 25), and thus, labor for adjusting the opening of the first restriction unit 76 to a maximum is saved and convenience is improved. In a case where the attachment and detachment detection unit 42 detects the size of the effective detection region 81 of the radiography unit 23 or in a case where the size of the effective detection region 81 of the radiography unit 23 can be detected by other methods, the drive controller 121 automatically drives the first restriction unit 76 according to the size of the effective detection region 81 of the radiography unit 23. That is, the drive controller 121 automatically conforms the irradiation range of the radiation to the size (including the shape) of the effective detection region 81 by driving the first restriction unit 76.

Figure 15:
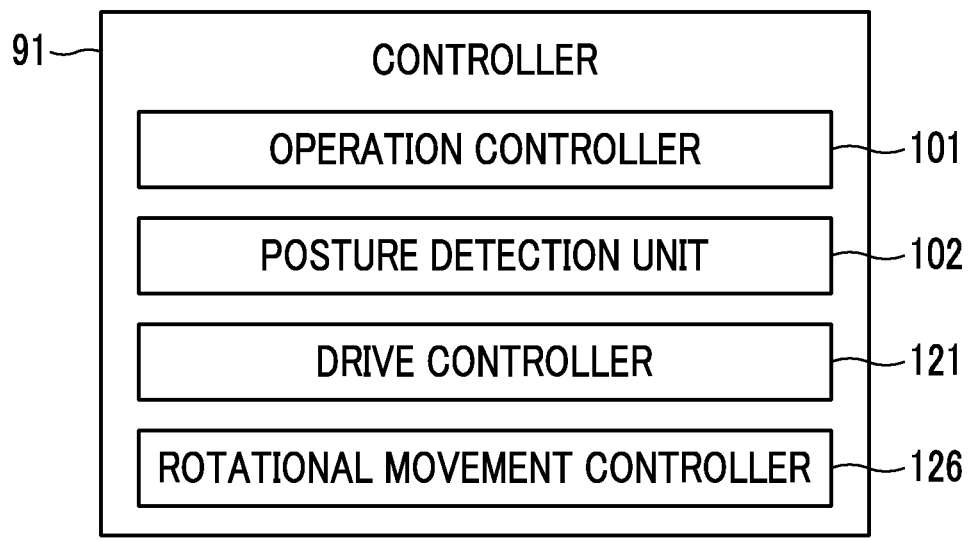
FIG. 15 is a block diagram of a controller having a rotational movement controller.

As shown in FIG. 15, the controller 91 can comprise a rotational movement controller 126 instead of the above-described operation controller 101 or the like or in addition to the operation controller 101 or the like.

Figure 16:
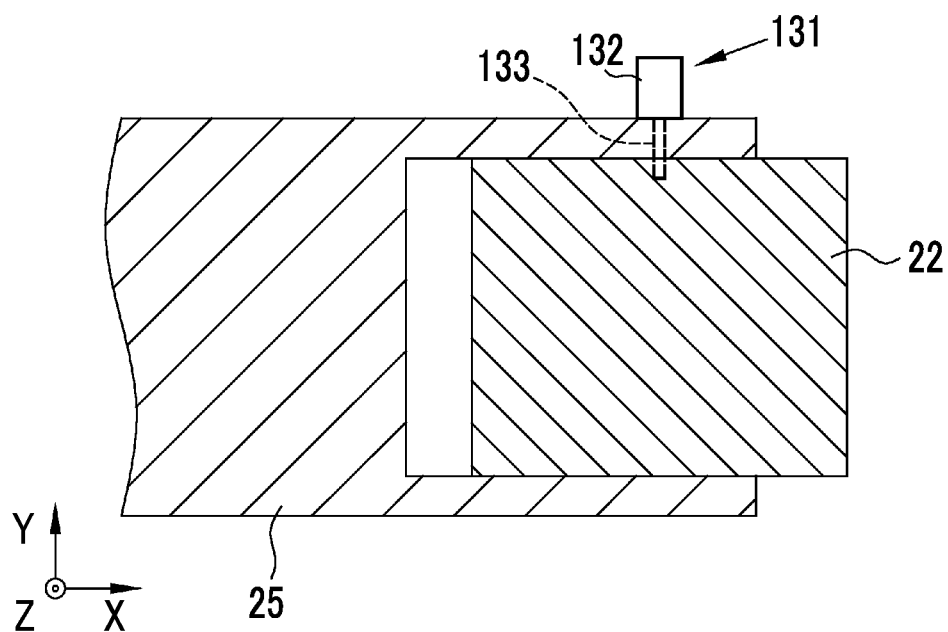
FIG. 16 is an explanatory view showing a locking mechanism of the radiation generation unit.

The rotational movement controller 126 validates or invalidates rotational movement with respect to the C-arm 25 as a support of the radiation generation unit 22. Specifically, as shown in FIG. 16, after the radiation generation unit 22 is attached to the C-arm 25, the rotational movement of the radiation generation unit 22 is locked using a locking mechanism 131. The locking mechanism 131 is, for example, an electromagnetic lock including a solenoid 132 and an iron core 133 that goes in and out the solenoid 132 by providing electric conduction to the solenoid 132 (or by cutting off electric conduction of the solenoid 132).

For example, in a case where the radiography unit 23 is detached from the C-arm 25, the rotational movement controller 126 performs control such that the locking mechanism 131 unlocks the rotational movement (validates the rotational movement) of the radiation generation unit 22. On the contrary, in a case where the radiography unit 23 is attached to the C-arm 25, the rotational movement controller 126 performs control such that the locking mechanism 131 locks the rotational movement (invalidates the rotational movement) of the radiation generation unit 22. In this way, in a case where the rotational movement of the radiation generation unit 22 is automatically validated or invalidated in conjunction with the attachment or detachment of the radiography unit 23, the radiation generation unit 22 may not be manually locked or unlocked, and thus, convenience is improved.

Figure 17:
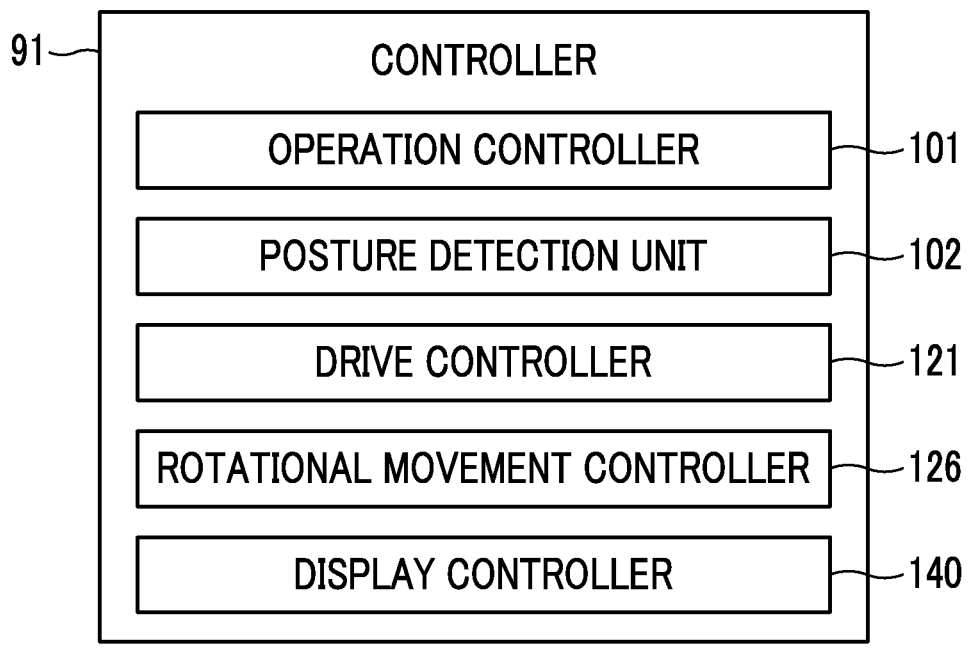
FIG. 17 is a block diagram of a controller having a display controller.

As shown in FIG. 17, the controller 91 can comprise a display controller 140 instead of the operation controller 101 or the like or in addition to the operation controller 101 or the like. The display controller 140 validates or invalidates the display of the irradiation range of the radiation by the irradiation range display unit 74 depending on the position of the radiation generation unit 22. For example, in a case where the radiation generation unit 22 is present vertically downward relatively to the radiography unit 23, the display controller 140 invalidates an operation (an operation to turn on the display of the irradiation range) of the first operating unit 41 regarding the irradiation range display unit 74. On the other hand, in a case where the radiation generation unit 22 is present vertically upward relatively to the radiography unit 23, the display controller 140 validates the operation of the first operating unit 41 regarding the irradiation range display unit 74. This is to reduce a possibility that light emitted from the irradiation range display unit 74 is incident directly on the eyes of the physician or the like, and to validate the display of the irradiation range as needed in a case where the display of the irradiation range can be performed safely.

Figure 18:
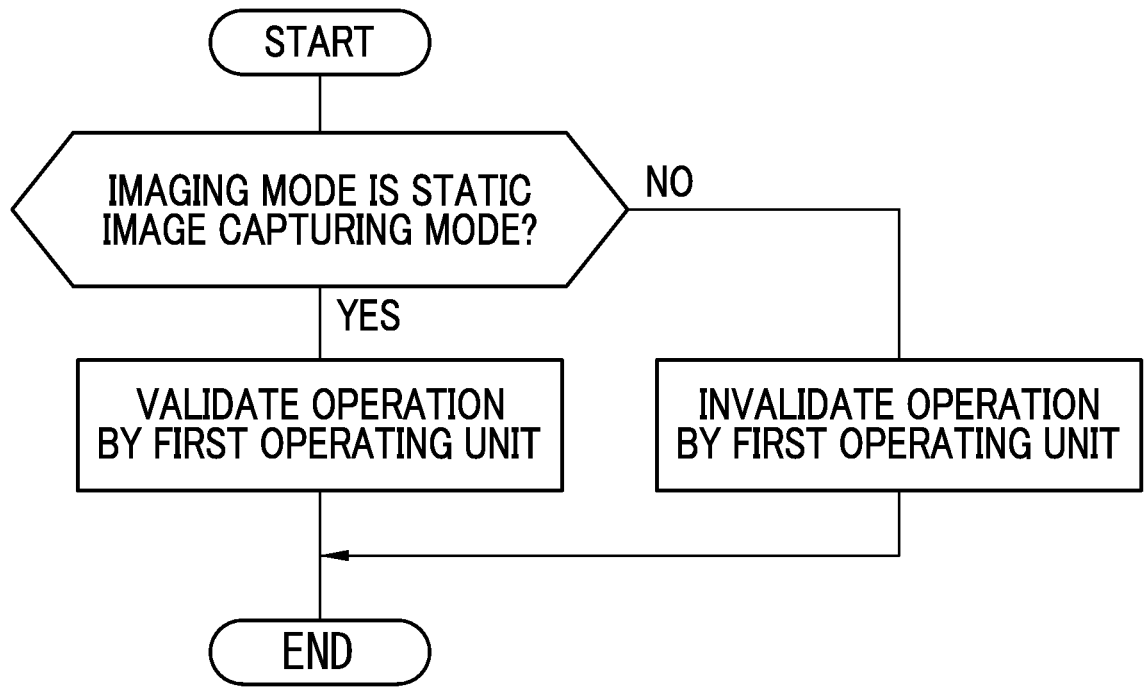
FIG. 18 is a flowchart showing a control aspect.

In the above-described embodiment, although the modification examples, and the like, the operation controller 101 validates or invalidates the operation by the first operating unit 41 depending on the position (in particular, a relative position to the radiography unit 23 in the vertical direction) of the radiation generation unit 22, the invention is not limited thereto. For example, in a case where a static image capturing mode in which the radiation generation unit 22 is disposed at a first position to capture a static image of the subject 15 and a video capturing mode in which the radiation generation unit 22 is disposed at a second position different from the first position to capture video of the subject 15 are provided, as shown in FIG. 18, the operation controller 101 can validate the operation of the collimator using the first operating unit 41 in a case of the static image capturing mode, and can invalidate the operation of the collimator using the first operating unit 41 in a case of the video capturing mode. That is, in this modification example, in a case where the imaging mode is associated with the position of the radiation generation unit 22, the validation and invalidation of the first operating unit 41 are switched depending on whether the imaging mode is the static image capturing mode or the video capturing mode, whereby the operation controller 101 can substantially validate or invalidate the operation of the collimator using the first operating unit 41 depending on the position of the radiation generation unit 22. In a case where the first position is present relatively vertically downward of the radiography unit 23, and the second position is present relatively vertically upward of the radiation generation unit 22, the same configuration as in the above-described embodiment is made.

In the above-described modification examples, although the validation and invalidation of the first operating unit 41 are switched depending on the imaging mode in a case where the imaging mode is associated with the position of the radiation generation unit 22, the radiography apparatus 10 can switch the validation and invalidation of the first operating unit 41 depending on the imaging mode even though the imaging mode is not associated with the position of the radiation generation unit 22. In this case, the operation controller 101 validates the operation of the collimator using the first operating unit 41 in a case of the static image capturing mode and invalidates the operation of the collimator 73 using the first operating unit 41 in a case of the video capturing mode without depending on the position or the like of the radiation generation unit 22. In this way, even in a case where the operation of the collimator 73 using the first operating unit 41 is validated or invalidated according to the classification of the imaging mode without depending on the position or the like of the radiation generation unit 22, the operation of the collimator 73 using the first operating unit 41 is automatically validated only when needed. Thus, an unintentional operation is prevented and convenience is improved.

Figure 19:
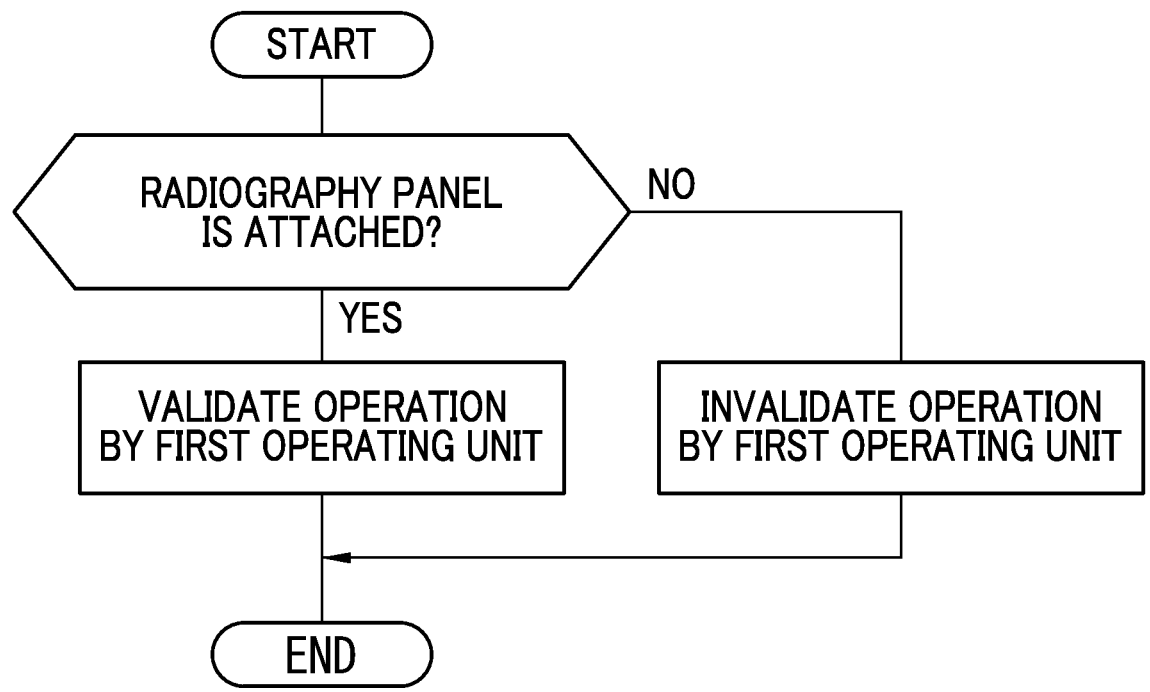
FIG. 19 is a flowchart showing a control aspect.

For example, as shown in FIG. 19, the operation controller 101 can invalidate the operation by the first operating unit 41 in a case where the radiography unit 23 is attached to the C-arm 25 as a support and can validate the operation by the first operating unit 41 in a case where the radiography unit 23 is not attached to the C-arm 25 as a support. On the contrary, the operation controller 101 can validate the operation by the first operating unit 41 in a case where the radiography unit 23 is attached to the C-arm 25 as a support and can invalidate the operation by the first operating unit 41 in a case where the radiography unit 23 is not attached to the C-arm 25 as a support. The attachment and detachment of the radiography unit 23 are associated with the validation and invalidation of the first operating unit 41, whereby it is possible to improve at least one of safety or convenience.

A part or all of the components of the above-described embodiment and the modification examples can be used in any combination.

The above-described embodiment and the like includes a method of operating a radiography apparatus including a radiation generation unit having a radiation source configured to generate radiation, a collimator configured to adjust an irradiation range of the radiation, and a first operating unit configured to operate the collimator, a radiography unit that images a subject using the radiation, a support that supports at least the radiation generation unit in a case where the subject is imaged, the method comprising, at an operation controller, a step of validating or invalidating an operation of the collimator using the first operating unit depending on a position of the radiation generation unit.

In the above-described embodiment, the hardware structures of processing units that execute various kinds of processing, such as the controller 91 and the respective units constituting the controller 91, are various processors described below. Various processors include a graphical processing unit (GPU), a programmable logic device (PLD) that is a processor capable of changing a circuit configuration after manufacture, such as a field programmable gate array (FPGA), a dedicated electric circuit that is a processor having a circuit configuration dedicatedly designed for executing various kinds of processing, and the like in addition to a central processing unit (CPU) that is a general-purpose processor executing software (program) to function as various processing units.

One processing unit may be configured of one of various processors described above or may be configured of a combination of two or more processors (for example, a plurality of FPGAs, a combination of a CPU and an FPGA, or a combination of a CPU and a GPU) of the same type or different types. A plurality of processing units may be configured of one processor. As an example where a plurality of processing units are configured of one processor, first, as represented by a computer, such as a client or a server, there is a form in which one processor is configured of a combination of one or more CPUs and software, and the processor functions as a plurality of processing units. Second, as represented by system on chip (SoC) or the like, there is a form in which a processor that implements all functions of a system including a plurality of processing units into one integrated circuit (IC) chip is used. In this way, various processing units may be configured using one or more processors among various processors described above as a hardware structure.

In addition, the hardware structures of various processors are, more specifically, electric circuits (circuitry), in which circuit elements, such as semiconductor elements, are combined.

EXPLANATION OF REFERENCES

10: radiography apparatus
11: imaging unit
12: display unit
15: subject
21: imaging unit body
22: radiation generation unit
23: radiography unit
25: C-arm
27: caster
31: cable
36: display unit body
37: monitor
41: first operating unit
42: attachment and detachment detection unit
51: sliding mechanism
52: lifting mechanism
61: second operating unit
71: drive circuit
72: radiation source
73: collimator
74: irradiation range display unit
75: mono-tank
76: first restriction unit
76a: first outer leaf blade
76b: second outer leaf blade
76c: third outer leaf blade
76d: fourth outer leaf blade
77: second restriction unit
77a: first inner leaf blade
77b: second inner leaf blade
77c: third inner leaf blade
77d: fourth inner leaf blade
78: radiation axis
79: first housing
80: second housing
81: effective detection region 82: irradiation range
86: radiography panel
87: grid
88: battery
91: controller
92: power supply unit
93: image processing unit
101: operation controller
102: posture detection unit
110: first potentiometer
120: second potentiometer
121: drive controller
126: rotational movement controller
131: locking mechanism
132: solenoid
133: iron core
140: display controller
Xc: arrow
Yc: arrow

What is claimed is:

1. A radiography apparatus comprising:
a radiation generation device having a radiation source configured to generate radiation, a collimator configured to adjust an irradiation range of the radiation, and a first operating device configured to operate the collimator;
a radiography device that images a subject using the radiation;
a support that supports at least the radiation generation device in a case where the subject is imaged; and
a processor configured to function as:
an operation controller that invalidates an operation of the collimator using the first operating device in a case where the radiation generation device is present vertically downward relatively to the radiography device, and validates the operation of the collimator using the first operating device in a case where the radiation generation device is present vertically upward relatively to the radiography device.

2. The radiography apparatus according to claim 1, wherein the processor is further configured to function as:
a posture detection unit that detects a posture of the support, and
wherein the operation controller obtains information regarding a position of the radiation generation device using a detection result of the posture detection unit.

3. The radiography apparatus according to claim 1, wherein the collimator comprises a first restriction member that restricts the irradiation range of the radiation, and a second restriction member that further restricts the irradiation range of the radiation restricted by the first restriction member, and
the first operating device operates the second restriction member.

4. The radiography apparatus according to claim 3, wherein the processor is further configured to function as:
a drive controller that automatically drives the first restriction member, and
wherein the drive controller relaxes the restriction of the irradiation range of the radiation by the first restriction member in a case where the operation controller validates the operation using the first operating device, compared to a case where the operation controller invalidates the operation using the first operating device.

5. The radiography apparatus according to claim 1, wherein a second operating device that operates the collimator is provided in a body to which the support is attached.

6. The radiography apparatus according to claim 1, wherein the processor is further configured to function as:
a rotational movement controller that validates or invalidates rotational movement of the radiation generation device with respect to the support.

7. The radiography apparatus according to claim 1, further comprising:
an irradiation range display device that displays the irradiation range of the radiation adjusted by the collimator using visible light, and
wherein the processor is further configured to function as:
a display controller that validates or invalidates the display of the irradiation range of the radiation by the irradiation range display device depending on a position of the radiation generation device.

8. A radiography apparatus comprising:
a radiation generation device having a radiation source configured to generate radiation, a collimator configured to adjust an irradiation range of the radiation, and a first operating device configured to operate the collimator;
a radiography device that images a subject using the radiation;
a support that supports at least the radiation generation device in a case where the subject is imaged; and
a processor configured to function as:
an operation controller that validates an operation of the collimator using the first operating device in a static image capturing mode where a static image of the subject is captured, and invalidates the operation of the collimator using the first operating device in a video capturing mode where video of the subject is captured.

9. The radiography apparatus according to claim 8, wherein the collimator comprises a first restriction member that restricts the irradiation range of the radiation, and a second restriction member that further restricts the irradiation range of the radiation restricted by the first restriction member, and
the first operating device operates the second restriction member.

10. The radiography apparatus according to claim 9, wherein the processor is further configured to function as:
a drive controller that automatically drives the first restriction member, and
wherein the drive controller relaxes the restriction of the irradiation range of the radiation by the first restriction member in a case where the operation controller validates the operation using the first operating device, compared to a case where the operation controller invalidates the operation using the first operating device.

11. The radiography apparatus according to claim 8, wherein a second operating device that operates the collimator is provided in a body to which the support is attached.

12. The radiography apparatus according to claim 8, wherein the processor is further configured to function as:
a rotational movement controller that validates or invalidates rotational movement of the radiation generation device with respect to the support.

13. The radiography apparatus according to claim 8, further comprising:
- an irradiation range display device that displays the irradiation range of the radiation adjusted by the collimator using visible light, and
- wherein the processor is further configured to function as:
  - a display controller that validates or invalidates the display of the irradiation range of the radiation by the irradiation range display device depending on a position of the radiation generation device.

14. A radiography apparatus comprising:
- a radiation generation device having a radiation source configured to generate radiation, a collimator configured to adjust an irradiation range of the radiation, and a first operating device configured to operate the collimator;
- a radiography device that images a subject using the radiation;
- a support that supports at least the radiation generation device in a case where the subject is imaged; and
- a processor configured to function as:
  - an operation controller that invalidates an operation by the first operating device in a case where the radiography device is attached to the support, and validates the operation by the first operating device in a case where the radiography device is not attached to the support.

15. The radiography apparatus according to claim 14, wherein the collimator comprises a first restriction member that restricts the irradiation range of the radiation, and a second restriction member that further restricts the irradiation range of the radiation restricted by the first restriction member, and the first operating device operates the second restriction member.

16. The radiography apparatus according to claim 15, wherein the processor is further configured to function as:
- a drive controller that automatically drives the first restriction member, and
- wherein the drive controller relaxes the restriction of the irradiation range of the radiation by the first restriction member in a case where the operation controller validates the operation using the first operating device, compared to a case where the operation controller invalidates the operation using the first operating device.

17. The radiography apparatus according to claim 14, wherein a second operating device that operates the collimator is provided in a body to which the support is attached.

18. The radiography apparatus according to claim 14, wherein the processor is further configured to function as:
- a rotational movement controller that validates or invalidates rotational movement of the radiation generation device with respect to the support.

19. The radiography apparatus according to claim 14, further comprising:
- an irradiation range display device that displays the irradiation range of the radiation adjusted by the collimator using visible light, and
- wherein the processor is further configured to function as:
  - a display controller that validates or invalidates the display of the irradiation range of the radiation by the irradiation range display device depending on a position of the radiation generation device.

* * * * *